(12) United States Patent
Chadha et al.

(10) Patent No.: US 10,393,746 B2
(45) Date of Patent: Aug. 27, 2019

(54) KIT FOR IMMUNOLOGICAL DETECTION OF TNF-ALPHA, STNFR1 AND IL-8 IN PROSTATE CANCER

(71) Applicant: Health Research, Inc., Buffalo, NY (US)

(72) Inventors: Kailash Chadha, Williamsville, NY (US); Willie Underwood, Williamsville, NY (US); Austin Miller, Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 15/992,567

(22) Filed: May 30, 2018

(65) Prior Publication Data

US 2018/0275130 A1 Sep. 27, 2018

Related U.S. Application Data

(62) Division of application No. 14/911,580, filed as application No. PCT/US2014/050709 on Aug. 12, 2014, now Pat. No. 9,995,748.

(60) Provisional application No. 61/864,718, filed on Aug. 12, 2013.

(51) Int. Cl.

| | |
|---|---|
| *C07K 16/24* | (2006.01) |
| *C07K 16/28* | (2006.01) |
| *C07K 16/30* | (2006.01) |
| *G01N 33/574* | (2006.01) |
| *G01N 33/53* | (2006.01) |
| *C07K 14/525* | (2006.01) |
| *C07K 14/715* | (2006.01) |
| *C07K 14/54* | (2006.01) |
| *C07K 14/47* | (2006.01) |
| *C07K 14/705* | (2006.01) |

(52) U.S. Cl.
CPC ..... *G01N 33/57434* (2013.01); *C07K 16/241* (2013.01); *C07K 16/244* (2013.01); *C07K 16/2875* (2013.01); *C07K 16/3069* (2013.01); *G01N 33/53* (2013.01); *C07K 14/4748* (2013.01); *C07K 14/525* (2013.01); *C07K 14/5415* (2013.01); *C07K 14/5421* (2013.01); *C07K 14/70578* (2013.01); *C07K 14/7151* (2013.01); *G01N 2333/525* (2013.01); *G01N 2333/5421* (2013.01); *G01N 2333/70578* (2013.01)

(58) Field of Classification Search
None
See application file for complete search history.

(56) References Cited

U.S. PATENT DOCUMENTS

| | | |
|---|---|---|
| 5,861,248 A | 1/1999 | Russell et al. |
| 2005/0265996 A1 | 12/2005 | Lentz |
| 2005/0272110 A1 | 12/2005 | Drukier |

FOREIGN PATENT DOCUMENTS

WO 98/36278 A1 8/1998

OTHER PUBLICATIONS

Jutley et al, 2000. Pediatr Surg Int. 16:64-68 (Year: 2000).*
Package Insert titled "Quantikine ELISA Human TNF-α Immunoassay", no author listed, published by R&D Systems, May 2012. (Year: 2012).*
Michalaki, V., et al., Serum levels of IL-6 and TNF-α correlate with clinicopathologocal features and patient survival in patients with prostate cancer, Br. J. Cancer, Jun. 14, 2004, vol. 90, No. 12, pp. 2312-2326.
Kyriakidis, I., et al., Serum TNF-alfpha, sTNFR1, IL-6, IL-8 and IL-10 levels in Weil's syndrome, Cytokine, Feb. 12, 2011, vol. 54, pp. 117-120.
Navarro, S.L., et al., Reliability of Serum Biomarkers of Inflammation from Repeated Measures in Healthy Individuals, Cancer Epidemiol Biomarkers Prev., May 7, 2012, vol. 21, No. 7, pp. 1167-1170.
Mustian, K.M., et al., Cytokine-mediated changes associated with improvements in cancer-related fatigue induced by exercise: Results from a randomized pilot study of cancer patients receiving radiotherapy, Journal of Clinical Oncology, 2009, vol. 27, No. 15s, pp. 516s.

* cited by examiner

*Primary Examiner* — Zachary C Howard
(74) *Attorney, Agent, or Firm* — Hodgson Russ LLP

(57) ABSTRACT

The disclosure provides methods of using biomarkers to improve diagnosis of forms of prostate. The method includes testing a biological sample from an individual for a interleukin-8 (IL-8), Tumor necrosis factor alpha (TNF-α) and soluble tumor necrosis factor-α receptor 1 (sTNFR1), and may further include testing for prostate serum antigen (PSA). Use of these markers in combination provides tests that are more sensitive and specific than PSA in differentiating benign versus malignant prostate disease and/or localized CaP versus metastatic CaP and show that the specificity and sensitivity of a PSA-based CaP diagnosis can be significantly enhanced by measuring IL-8, TNF-α and sTNFR1.

3 Claims, 3 Drawing Sheets

KIT FOR IMMUNOLOGICAL DETECTION OF TNF-ALPHA, STNFR1 AND IL-8 IN PROSTATE CANCER

CROSS REFERENCE TO RELATED APPLICATIONS

This application is a divisional of U.S. patent application Ser. No. 14/911,580, filed Feb. 11, 2016, which is a National Phase of International Patent Application No. PCT/US2014/050709, filed Aug. 12, 2014, which claims priority to U.S. Provisional Patent Application No. 61/864,718, filed Aug. 12, 2013, the disclosures of each of which are incorporated herein by reference.

STATEMENT REGARDING FEDERALLY SPONSORED RESEARCH

This invention was made with government support under CA113950 awarded by the National Institutes of Health. The government has certain rights in the invention.

FIELD

The present disclosure relates generally to cancer detection and more specifically for compositions and methods related to diagnosis of prostate cancer.

BACKGROUND

According to the American Cancer Society, an estimated 240,890 new cases of prostate Cancer (CaP) will be diagnosed and 33,720 men will die of CaP in 2012. There is a great deal of controversy regarding the widespread use of Prostate Specific Antigen (PSA) testing for the diagnosis of CaP. The adoption of PSA testing has been credited with the significant decline in the proportion of men diagnosed with metastatic disease and the overall CaP mortality over the last two decades. However, PSA testing has been criticized for lacking the specificity to adequately differentiate between men with and without CaP. Also, many men diagnosed with CaP have a normal PSA. Conversely, elevated PSA levels have been found in other diseases including breast cancer, renal cell carcinoma, ovarian cancer and adrenal neoplasm. The widespread use of PSA testing is reported to have resulted in unnecessary prostate biopsies, and the over diagnosis and treatment of indolent CaP. According to some opponents, PSA testing does not improve CaP survival, and may be harmful to men (physically and psychologically) and to society (increasing the cost of health care without a survival benefit). Despite several strategies to enhance the specificity of PSA (e.g. PSA density, PSA-velocity, age adjusted PSA ranges and free to total PSA ratios), PSA testing remains a controversial tool for the early detection of CaP. At present, no commercially available biomarker(s) have been identified to differentiate between men with and without and CaP, or to differentiate high risk CaP from indolent CaP. Clearly, much benefit would be derived from a serological test that more accurately identifies early stage prostate cancers, or correctly distinguishes between men with non-cancerous and cancerous conditions, or differentiates men with high risk CaP from those with indolent disease. The present disclosure meets these and other needs.

SUMMARY

The present disclosure provides compositions and methods for determining prostate cancer, and biomarkers that are useful for distinguishing forms of prostate cancer from one another. The method generally comprises testing a biological sample from an individual for a combination of biomarkers selected from interleukin-8 (IL-8), Tumor necrosis factor alpha (TNF-α) and soluble tumor necrosis factor-α receptor 1 (sTNFR1), and may further comprise testing for prostate serum antigen (PSA). The disclosure provides for using combinations of these biomarkers to provide tests that are more sensitive and specific than PSA in differentiating benign versus malignant prostate disease and/or localized CaP versus metastatic CaP. Results presented in this disclosure accordingly demonstrate that the specificity and sensitivity of a PSA-based CaP diagnosis can be significantly enhanced by concurrent measurements of one or more of IL-8, TNF-α and sTNFR1.

In one aspect the disclosure includes improving a diagnosis of: i) an individual who has elevated PSA, but also has a prostate biopsy that is negative for prostate cancer (a condition referred to herein as "elPSA_negBx"), ii) an individual who has localized CaP; iii) an individual who has metastatic CaP, and iv) an individual who has castration resistant prostate cancer (CRPC). In embodiments, the amount of each of L-8, TNF-α and sTNFR1 is tested and compared to a reference to provide a diagnosis, or to aid in the diagnosis, of a form of prostate cancer, or that an individual does not have prostate cancer. In embodiments, the disclosure provides a method for improved distinction between localized CaP and elPSA_negBx, and for improved distinction between localized versus metastatic CaP.

DESCRIPTION

Figure 1:
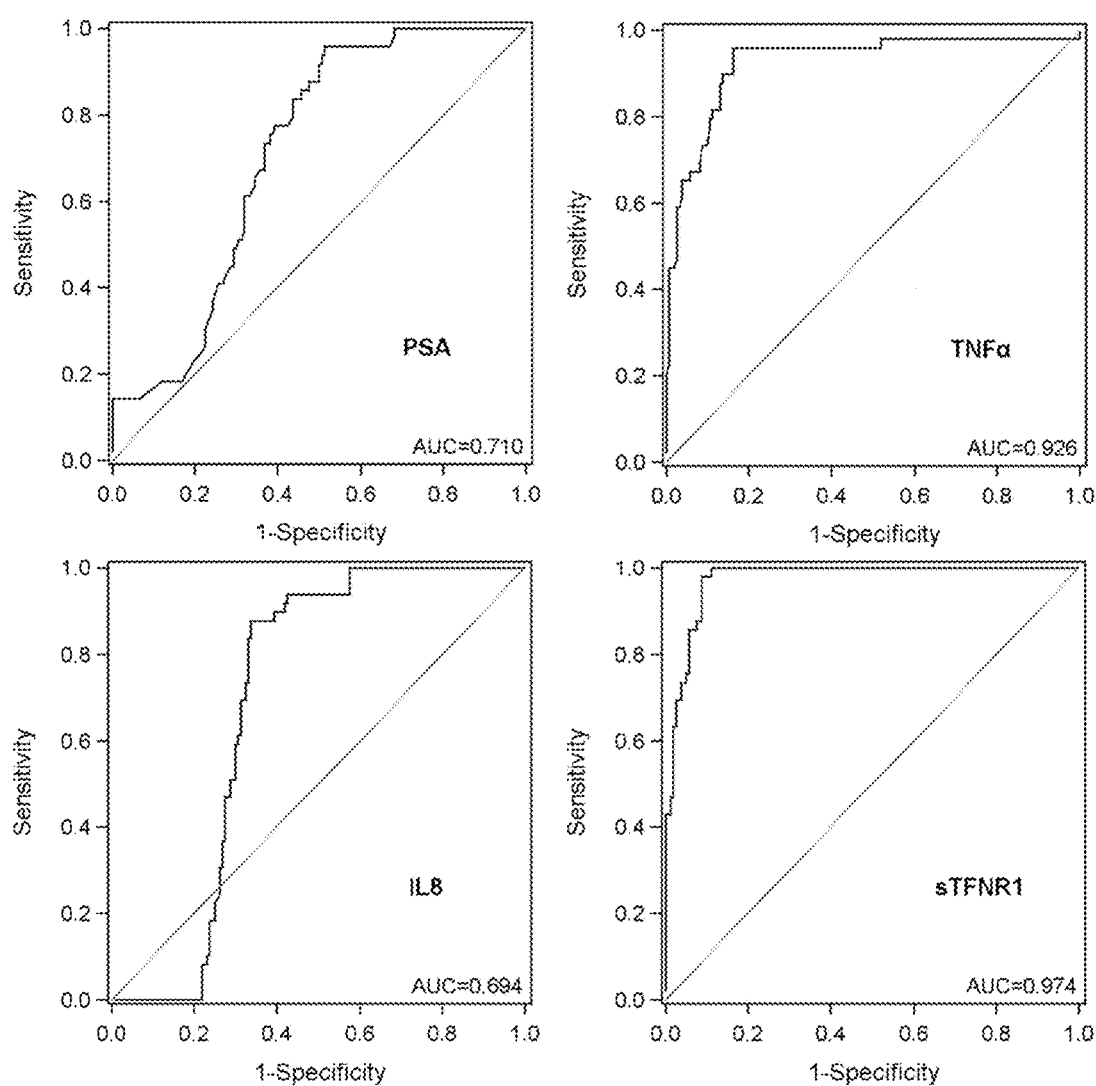
FIG. 1 provides graphical depictions of data depicting the probability of distinguishing elPSA_negBx subjects from CaP. This measure is equivalent to the area under the Receiver Operating Characteristic curve (AUC). The strongest predictor of not having CaP is log (sTNFr1) with AUC=0.97, followed closely by log(TNF α) with AUC=0.93.

The present disclosure provides compositions and methods useful for diagnosis and/or aiding in the diagnosis of prostate cancer and in general is based at least in part on our discovery that an ensemble of particular biomarkers is superior to previously available reagents for diagnosis, staging, and aiding in treatment decisions for individuals who have, are suspected of having, or are at risk for development or recurrence of prostate cancer.

In particular, the present disclosure in various aspects uses concurrent serum measurements of IL-8, TNF-α and its soluble receptor (sTNFR1) in normal healthy individuals (controls), patients with elevated PSA but a negative prostate biopsy (elPSA_negBx), patients diagnosed with localized CaP, and patients with castration resistant prostate cancer (CRPC) to establish threshold levels of these biomarkers for use in prostate cancer diagnosis. While previous reports disclose a relationship between serum IL-8 and TNF-α measurements in the diagnosis of CaP, there has been no demonstration of the use of these biomarkers to enhance the sensitivity and specificity of PSA. Thus, in one aspect, the present disclosure demonstrates that the specificity and sensitivity of a PSA-based CaP diagnosis can be significantly enhanced by concurrent serum measurements of IL-8, TNF-α, sTNFR1, and combinations thereof.

In particular embodiments, the present disclosure comprises detecting in a sample from an individual the presence or absence, and/or the amount, of any one or any combination of IL-8, TNF-α and TNFR1 and PSA (each referred to herein individually as a biomarker). In certain embodiments, each of IL-8, TNF-α and TNFR1 are determined. In certain embodiments, each of IL-8, TNF-alpha and TNFR1 and PSA are determined. In embodiments, any combination of the biomarkers may comprise the only biomarkers determined in order to test a sample in connection with diagnosis, or to aid in diagnosis, or staging, or monitoring treatment of prostate cancer. The disclosure includes excluding any individual biomarker or combination of biomarkers from the method, provided at least one biomarker disclosed herein is determined.

Quantitative or qualitative determinations of the amount of each biomarker in a sample according to the present disclosure can be measured and/or compared against any suitable reference, such as an established normal range, a standardized curve, positive, negative, or matched controls, etc. In embodiments, the amount of each biomarker is compared to normal (i.e., non-prostate cancer) control, or a control with a known prostate cancer diagnosis. In certain aspects, the amount of biomarker is determined in view of a reference in the form of area under a receiver operating characteristic (ROC) curve (AUC). In embodiments, AUC values can range from 0.5 (indicating no discriminating ability) to 1.0 (indicating perfect discrimination), inclusive, and including all digits between 0.5 to 1.0, to the third decimal place. In embodiments presented herein, AUC values greater than 0.8 are considered to be useful in predicting outcomes for individual patients. In specific embodiments as described further in the Examples presented herein, we demonstrate that TNF-α (AUC=0.93) and sTNFR1 (AUC=0.97) are strong predictors of elPSA_negBx (vs malignant), and that the sensitivity/specificity profiles of TNF-α and sTNFR1 are uniformly superior to those of PSA. The best predictor of elPSA_negBx vs malignant disease was sTNFR1 and IL8 combined (AUC=0.997). The strongest single predictors of localized versus metastatic CaP were TNF-α (AUC=0.992) and PSA (AUC=0.963) levels. Thus, combinations of these biomarkers as further described herein are more sensitive and specific than using PSA alone. In embodiments, the disclosure comprises an approach for aiding in distinguishing between metastatic or localized prostate cancer, and for distinguishing between localized prostate cancer and benign prostate disease. In one embodiment, the disclosure provides for distinguishing in metastatic or localized prostate cancer in an individual known or suspected to have one of these conditions. This approach comprises testing a biological sample from the individual to determine interleukin-8 (IL-8), Tumor necrosis factor alpha (TNF-α) and soluble tumor necrosis factor-α receptor 1 (sTNFR1) in the sample, wherein determining IL8 to be equal to or greater than 5.1 pg/ml, TNFa to be equal to or greater than 3.1 pg/ml and sTFNr1 to be equal to or greater than 513.9 pg/ml aids in a diagnosis that that the individual has the metastatic disease. In another aspect, the disclosure provides for distinguishing localized prostate cancer from a benign form of prostate disease. This approach comprises testing a biological sample from the individual to determine the IL-8, TNF-α and the sTNFR1, wherein determining an amount of TNFa of equal to or greater than 1.2 pg/ml and sTFNr1 in an amount equal to or greater than 729 pg/ml aids in a diagnosis that the individual has the localized prostate cancer.

The invention is generally suitable for use with any biological sample obtained from an individual, including but not necessarily limited to tissue biopsies (i.e., prostate/tumor tissue), blood, urine, or plasma. In certain embodiments, the sample comprises serum. Any suitable techniques can be used to obtain such biological samples. The biological sample can be tested directly, or it can be subjected to a processing step to isolate, amplify or purify components of the sample before testing.

In certain embodiments, the sample is obtained from an individual who has previously been tested for PSA and/or has been diagnosed with any form of or risk for developing prostate cancer based on a PSA test. In embodiments, a sample tested in the method of the present disclosure is obtained from an individual who has been previously determined to have elevated PSA, or to have normal PSA. The sample may be obtained from an individual who has been previously determined to have a benign prostate condition, including but not necessarily limited to benign prostatic hyperplasia (BPH) or any other non-malignant prostate tumor. In embodiments, the sample may be obtained from an individual who is undergoing prostate cancer therapy. Thus, multiple measurements can be obtained prior to, during, and/or subsequent to prostate cancer therapy to, for example, monitor the progression of the disease and/or the efficacy of any particular therapeutic approach. In embodiments, the invention also facilitates the diagnosis that a prostate tumor is benign.

Each of the biomarkers disclosed herein can be ascertained from the biological sample using established techniques. In general, each biomarker will be determined using immunological-based approaches, such as any form of ELISA assays. In embodiments, TNF-α will be detected using a method having sensitivity in the range of 0.5 to 32 pg/ml. sTNFR1 will be detected using a method having sensitivity range of 10 to 1000 pg/ml. Human IL-8 will be detected using a method having sensitivity in the range of 5 to 100 pg/ml. Each of these ranges as well as all other ranges herein are inclusive of each endpoint, and include all digits there between, as well as all sub-ranges there between.

In embodiments, the present disclosure includes obtaining a biological sample from an individual, mixing the biological sample with specific binding partners which will recognize the biomarkers described herein, and detecting the specific binding partner bound directly or indirectly to the biomarker. Thus the invention comprises detecting complexes of specific binding partners. Detection of the complexes can aid in the diagnosis of a disease. In embodiments, the presence or absence of complexes is a diagnosis. In embodiments, the specific binding partners comprise antibodies, or antigen binding fragments thereof. Directly or indirectly determining the presence of a specific binding partner bound to the biomarker and quantifying the amount of biomarker can comprise a diagnosis of any stage or type of prostate cancer as further described herein, or can comprise a determination that the individual from whom the tested sample was obtained does not have prostate cancer or other prostate condition(s). In embodiments, the disclosure includes determining that an individual is elPSA_negBx, or has malignant disease, or has localized CaP, or has metastatic CaP. In an embodiment, determining that TNF-α

(AUC=0.93) and sTNFR1 (AUC=0.97) vs. malignant comprises a diagnosis of elPSA_negBx. In another embodiment, determining elPSA_negBx comprises determining sTNFR1 and IL8 combined (AUC=0.997). In embodiments, determining localized versus metastatic CaP comprises determining TNF-α (AUC=0.992) and PSA (AUC=0.963) levels. In embodiments, the disclosure includes making a diagnosis and/or aiding in diagnosis and/or distinguishing individuals who have and who do not have PCa using combinations of markers and AUC values as disclosed in Table 2 below, and/or as illustrated in FIG. 1. In embodiments, the disclosure includes making a diagnosis and/or aiding in diagnosis and/or distinguishing individuals who have and who do not have localized and metastatic PCa using combinations of markers and AUC values as disclosed in Table 3 and/or FIG. 2 below. Data presented in FIG. 1, and in Tables 1-6 also described in Example 7. In embodiments, articles of manufacture or kits comprising the specific binding partners are provided. In an embodiment, the disclosure includes a kit that comprises reagents for use in immunological detection of TNF-α, sTNFR1 and IL-8. In embodiments, the kit comprises sealed containers that comprise monoclonal and/or polyclonal antibodies that are specific for the biomarkers. In an embodiment, the kit comprises anti-biomarker monoclonal or polyclonal antibodies that are covalently or non-covalently attached to a substrate, such as a multi-well plate, including but not necessarily a 96-well plate. In embodiments, the reagents are configured for use in an ELISA assay. In embodiments, the ELISA assay is a sandwich assay. In an embodiment, monoclonal and/or polyclonal anti-biomarker antibodies are included for us as detection antibodies. The antibodies can be modified or unmodified. In embodiments, the antibodies are modified so as to be conjugated to a moiety that is suitable for producing a visually detectable signal, such as a colorimetric signal for use in, for example, a quantitative ELISA assay. In embodiments, the detection antibody is conjugated to horseradish peroxidase. In embodiments, the kit is configured for a multiplex assay such that all three biomarkers can be analyzed concurrently using a single patient sample. In embodiments, the three biomarkers disclosed herein are the only biomarkers that the kit is configured to test. In embodiments the kit further comprises printed matter which includes an indication that the kit is to be used for diagnosing or aiding in the diagnosis of a prostate condition as described herein. In an embodiment, the printed material conveys information that an amount of IL8 that is equal to or greater than a reference amount, that an amount of TNFa equal to or greater than a reference amount, and that an amount of sTFNr1 equal to or greater than a reference amount, aids in a diagnosis that that the individual has the metastatic disease, or that an amount of TNFa equal to or greater than a reference amount and sTFNr1 in an amount equal to or greater than a reference amount aids in a diagnosis that the individual has the localized prostate cancer. In embodiments, the printed material is provided on a sheet of paper, plastic, cardboard or the like. In embodiments, the printed material is provided as a card included with the kit.

In embodiments, the present invention comprises fixing the determination of the biomarkers as disclosed herein in a tangible medium of expression, such as a compact disk, a DVD, or any other form of electronic file. Thus, tangible forms of media comprising a biomarker determination as set forth herein are included in the present disclosure. In embodiments, the invention includes communicating or otherwise transferring the tangible medium comprising the diagnostic determination to a health care provider, such as by electronically transmitting a file containing the determination to the health care provider.

In embodiments, the present disclosure comprises recommending a treatment protocol to an individual based at least in part on a diagnosis made by determining one or more biomarkers as described herein. In embodiments, the disclosure comprises determining the individual from whom a sample was tested has a form of prostate cancer, and recommending a surgical intervention, or a chemotherapeutic and/or androgen deprivation therapy for the individual. In embodiments, the method further comprises treating the individual based on a determination of biomarkers as described herein.

The following Examples are meant to illustrate but not limit the invention.

Example 1

This Example provides a description of the materials and methods used to obtain the results presented in the Example(s) that follow it.

Participant Privacy Protection.

Samples and patient data were provided from four sources with approved IRB protocols: (1) the Roswell Park Cancer Institute's (RPCI) Data Bank BioRepository (DBBR). (2) RPCI Screen Clinic and Urology Clinic; (3) Participating urologists in the Western New York community; and (4) The Cancer and Leukemia Group B; NCI protocol # CALGB-150201. All donor blood samples were de-identified to ensure participant confidentiality.

Patient Samples

Serum cytokine measurements were obtained from four comparison groups:

Controls.

Serum samples from 46 healthy males and 4 healthy females with no prior history of cancer at the time of collection were obtained from the RPCI-DBBR. Two participants were African American and 48 were Caucasian. Median age of this group was 43.5 years (range: 23 to 60).

Elevated PSA with Negative Biopsy (elPSA_negBx).

Serum samples from men (n=50) with confirmed PSA>4 ng/dl who received a negative trans-rectal ultrasound 12 core biopsy of the prostate. The participants were recruited by the Urology clinic at RPCI and by the participating Urologists in the Buffalo, N.Y. community. Six participants were African American and 44 were Caucasian. Median age was 69 years (range: 55 to 81).

Localized Prostate Cancer (Localized CaP).

Serum samples from 49 patients with localized CaP were provided by the RPCI-DBBR. These men had no therapy for clinically localized disease when samples were obtained. Median age of this group was 64 years (range: 46-85). Forty participants were Caucasian and nine were African American. Median Gleason score was 6 (range: 6 to 9);

Castration Resistant Prostate Cancer (CRPC).

Serum samples from 109 castration resistant prostate cancer (CRPC) patients were provided by the Cancer and Leukemia Group B; NCI protocol # CALGB-150201. The sample was restricted to include subjects with (1) histologically documented adenocarcinoma of the prostate, (2) metastatic disease with tumor progression after hormonal therapy[18] and (3) at least 4 weeks of androgen deprivation therapy. For patients with measurable disease, progression was defined as a greater than 25% increase in the sum of the products of the perpendicular diameters of all measurable lesions. For patients with "bone only" disease, a PSA greater than 5 ng/mL, which had risen from baseline on at least two successive occasions at least 4 weeks apart was required. All CRPC patients had metastatic disease demonstrated on imaging at some point during their history, but not necessarily at the time of enrollment. Patients were excluded if they had received prior chemotherapy, immunotherapy, experimental therapy, or prior treatment with ketoconazole, aminoglutethimide, or corticosteroids if they had a CALGB performance status of more than 2. Because of potential interactions with ketoconazole, no ongoing or concurrent use of terfenadine, astemizole, or cisapride was allowed. The median age was 72.3 years (range: 49 to 88). Among this group 82% were Caucasian, 16% were African-American and 2% were of another race. Nearly 89% participants had Gleason score in range of 5 to 10.

Each participant was classified as control, elPSA_negBx, localized CaP or CRPC by the participating physicians using established criterion. The participating physicians also determined if any individual, because of other medical reason(s), may not be the suitable candidate to participate in this study. Venous blood was drawn into vaccutainer tubes by trained technicians in respective clinics. The blood was allowed to clot at room temperature for one hour; spun at 2000 rpm for 15 minutes. Different aliquots (200 μl) of each serum sample were frozen at −70° C. until assayed. Each aliquot was thawed once and discarded after use.

Monitoring of Biomarkers.

TNF-α, soluble receptor for TNF-α (sTNFR1), and IL-8 measurements were made on each serum sample using highly sensitive commercially available ELISA kits. Ultrasensitive human TNF-α ELISA kit (Cat # KHC 3013) was purchased from BioSource International, Inc; Camarillo, Calif. It has the sensitivity range of 0.5 to 32 pg/ml. sTNFR1 ELISA kit (Cat # DY-225) was purchased from R & D Systems, Minneapolis, Minn. It has the sensitivity range of 10 to 1000 pg/ml. Human IL-8 ELISA kit (Cat #555244) was purchased from B.D. Biosciences, San Diego, Calif. It has the sensitivity range of 5 to 100 pg/ml. PSA levels were measured in all serum samples by ELISA as described before.[19] Commercially available standards were used in all cases. All instructions from manufacturers were strictly followed and inter and intra variations in assays were within the recommended limits. Standard curve and concentrations of each marker were calculated using the KC Junior (Bio-Tek, Inc) software.

Statistical Analysis:

The analyte expression measures were summarized using descriptive statistics (proportions, median, inter-quartile range (IQR)) within participant disease categories. Kruskal-Wallis tests were used for a global assessment of possible differences in the distributions of the analyte measures across the four disease categories. Following the statistically significant global test, six Wilcoxon Rank Sum Tests were used to test pairwise differences between groups for each analyte. Associations between the expression measurements were assessed conditionally (within disease categories) using Spearman Correlation coefficients. Within the CRPC patients, Wilcoxon Rank Sum Tests were done to assess analyte expression differences across dichotomized Gleason score and performance status categories.

To assess the ability of the measured analytes to distinguish between benign vs malignant, patients with localized CaP and CRPC groups were combined into a single "malignant" group, and compared to the elPSA_negBx patients. The predicted probability of benign (vs malignant) disease was modeled as a function of each log-transformed analyte using univariable and multivariable logistic regression methods. Multivariable models included more than one analyte, but did not adjust for other baseline characteristics. The modeling methods were also used to assess the ability of these markers to separate localized CaP and CRPC patients. The receiver operating characteristic (ROC) curve provides a visual indication of the predictive accuracy of the model, plotting Sensitivity (or true positive fraction) as a function of 1-Specificity (or false positive fraction) at different marker cutoff values. The probability of concordance between the predicted probability and observed disease state is a useful measure of discriminative accuracy. This measure is equivalent to the area under the ROC curve (AUC). The AUC values range from 0.5 (indicating no discriminating ability) to 1.0 (indicating perfect discrimination). For this analysis, AUC values greater than 0.8 were considered as useful in predicting outcomes for individual patients.

All p-values are two-sided and values <=0.05 were considered statistically significant. 95% confidence intervals describe the plausible range of values for the associated (true, unknown) parameter in the population. All analyses were performed using SAS version 9.2 (SAS, Cary N.C.).

Example 2

This Example provides a description of results obtained using the materials and methods described in Example 1.

Patient demographic and disease characteristics are summarized in Table 1.

TABLE 1

|  | Controls (n = 46) | elPSA_negBx (n = 50) | Localized CaP patients (n = 49) | CRPC patients (n = 109) |
|---|---|---|---|---|
| Age in years, median (IQR) | 47 (37-51.2) | 69 (61-73) | 64 (60-70) | 72 (66-78) |
| Race, n (%) | | | | |
| Caucasian | 44 (96%) | 44 (88%) | 40 (82%) | 89 (82%) |
| African-American | 2 (4%) | 6 (12%) | 9 (18%) | 17 (16%) |
| Other | | | 0 | 3 (2%) |
| Years Since Diagnosis | | | | |
| Median (IQR) | | | 0.2 (0.1-0.4) | 4.5 (2.0-6.9) |
| Gleason Score, n (%) | | | | |
| 2-4 | | | 0 | 9 (8%) |
| 5-7 | | | 41 (84%) | 56 (51%) |

TABLE 1-continued

|  | Controls (n = 46) | elPSA_negBx (n = 50) | Localized CaP patients (n = 49) | CRPC patients (n = 109) |
|---|---|---|---|---|
| 8-10 |  |  | 7 (14%) | 41 (38%) |
| Unknown |  |  | 1 (2%) | 3 (3%) |
| Performance status, n (%) |  |  |  |  |
| 0 | n/a | n/a | n/a | 61 (56%) |
| 1 |  |  |  | 36 (33%) |
| 2 |  |  |  | 9 (8%) |
| 3 |  |  |  | 1 (1%) |
| Disease Measurability, n (%) |  |  |  |  |
| Measurable | n/a | n/a | n/a | 40 (37%) |
| Evaluable |  |  |  | 65 (60%) |
| Unknown |  |  |  | 4 (3%) |
| Metastases, n (%) |  |  |  |  |
| Any | 0 | 0 | 0 | 102 (94%) |
| Visceral |  |  |  | 8 (7%) |
| Bone |  |  |  | 87 (80%) |
| Median PSA (ng/ml) IQR ($25^{th}$, $75^{th}$) | 1.39 (1.10, 1.96) | 3.80 (2.70, 5.48) | 2.40 (2.20, 3.10) | 16.40 (8.20, 30.00) |
| Median IL-8 (pg/ml) IQR ($25^{th}$, $75^{th}$) | 4.00 (3.33, 4.78) | 8.127 (6.86, 9.88) | 16.90 (11.60, 31.40) | 43.50 (15.00, 110.70) |
| Median TNF-α (pg/ml) Median IQR ($25^{th}$, $75^{th}$) | 5.12 (4.52, 5.83) | 1.15 (0.83, 1.74) | 2.20 (1.58, 2.62) | 5.50 (4.60, 6.50) |
| Median sTNFR1(pg/ml) Median IQR ($25^{th}$, $75^{th}$) | 670.37 (612.50, 777.89) | 585.00 (464.00, 710.00) | 978.40 (761.90, 1186.00) | 1790.20 (1431.20, 2609.20) |

This example sample included 250 participants (50 controls, 50 elPSA_negBx, 49 localized CaP, and 109 CRPC). In all 4 groups, a majority of the men were White. With a median age 43 years, men in the control group tended to be younger than men in the other groups (elPSA_negBx 69 years, localized CaP age 64 years and CRPC 72 years). The median PSA levels differed significantly between the control group (1.39 ng/ml), elPSA_negBx (3.80 ng/ml), localized CaP (2.40 ng/ml), and CRPC (16.40 ng/ml). The median PSA of the study groups were significantly higher than the control group ($p<0.05$). In addition, pairwise comparisons of PSA demonstrated each group was significantly different from each other (all tests p-values $<0.001$). The median IL-8 levels differed significantly ($p<0.001$) between the control group (4.00 pg/ml), elPSA_negBx (8.13 pg/ml), localized CaP (16.90 pg/ml), and CRPC patients (43.50 pg/ml). The median TNF-α levels differed significantly ($p<0.05$) between the control group (5.12 pg/ml) and elPSA_negBx (1.15 pg/ml), localized CaP (2.20 pg/ml). However the median TNF-α level was not significantly different between the control patients (5.12 pg/ml) and CRPC patients (5.50 pg/ml). The median sTNFR1 levels were significantly different between the control patients (670.37 pg/ml) and CRPC patients (1790.20 pg/ml) ($p<0.05$). However, the median sTNFR1 levels were not significantly different between the control group (670.37 pg/ml) and elPSA_negBx (585.00 pg/ml), localized CaP (978.40 pg/ml) groups. Significant differences for the median sTNFR1 levels were noted between the elPSA_negBx and the localized CaP and CRPC patients, as well as between the localized CaP and CRPC patients.

The ability of single analytes to distinguish between elPSA_negBx and malignant patients is illustrated in FIG. 1. TNF-α (AUC=0.93) and sTNFR1 (AUC=0.97) were strong predictors of elPSA_negBx (vs malignant). Comparing the ROC curves in FIG. 1, the sensitivity/specificity profiles of TNF-α and sTNFR1 are uniformly superior to those of PSA. AUC results (with 95% confidence intervals) for additive combinations of these biomarkers are shown in Table 2.

TABLE 2

AUC (95% CI) estimates for individual biomarkers and their combinations to distinguish between localized CaP and elPSA_negBx.

| Markers | AUC (95% CI) |
|---|---|
| PSA | 0.707 (0.599 to 0.815) |
| IL-8 | 0.807 (0.701 to 0.912) |
| TNF-α | 0.822 (0.739 to 0.905) |
| sTNFR1 | 0.906 (0.850 to 0.962) |
| TNF-α & sTNFR1 | 0.912 (0.859 to 0.966) |
| TNF-α & PSA | 0.836 (0.755 to 0.917) |
| TNF-α & IL-8 | 0.853 (0.775 to 0.932) |
| sTNFR1 & PSA | 0.926 (0.876 to 0.975) |
| sTNFR1 & IL-8 | 0.988 (0.974 to 1.000) |
| PSA & IL-8 | 0.796 (0.695 to 0.896) |
| TNF-α & sTNFR1 & PSA | 0.931 (0.885 to 0.978) |
| TNF-α & sTNFR1 & IL-8 | 0.988 (0.974 to 1.000) |
| TNF-α & PSA & IL-8 | 0.867 (0.793 to 0.942) |
| sTNFR1 & PSA & IL-8 | 0.989 (0.976 to 1.000) |
| TNF-α & sTNFR1 & PSA & IL-8 | 0.991 (0.979 to 1.000) |

The best predictor of elPSA_negBx vs malignant disease was sTNFR1 and IL8 combined (AUC=0.997). Adding more analytes to the combination of sTNFR1 and IL8 did not improve the biostatical accuracy.

Figure 2:
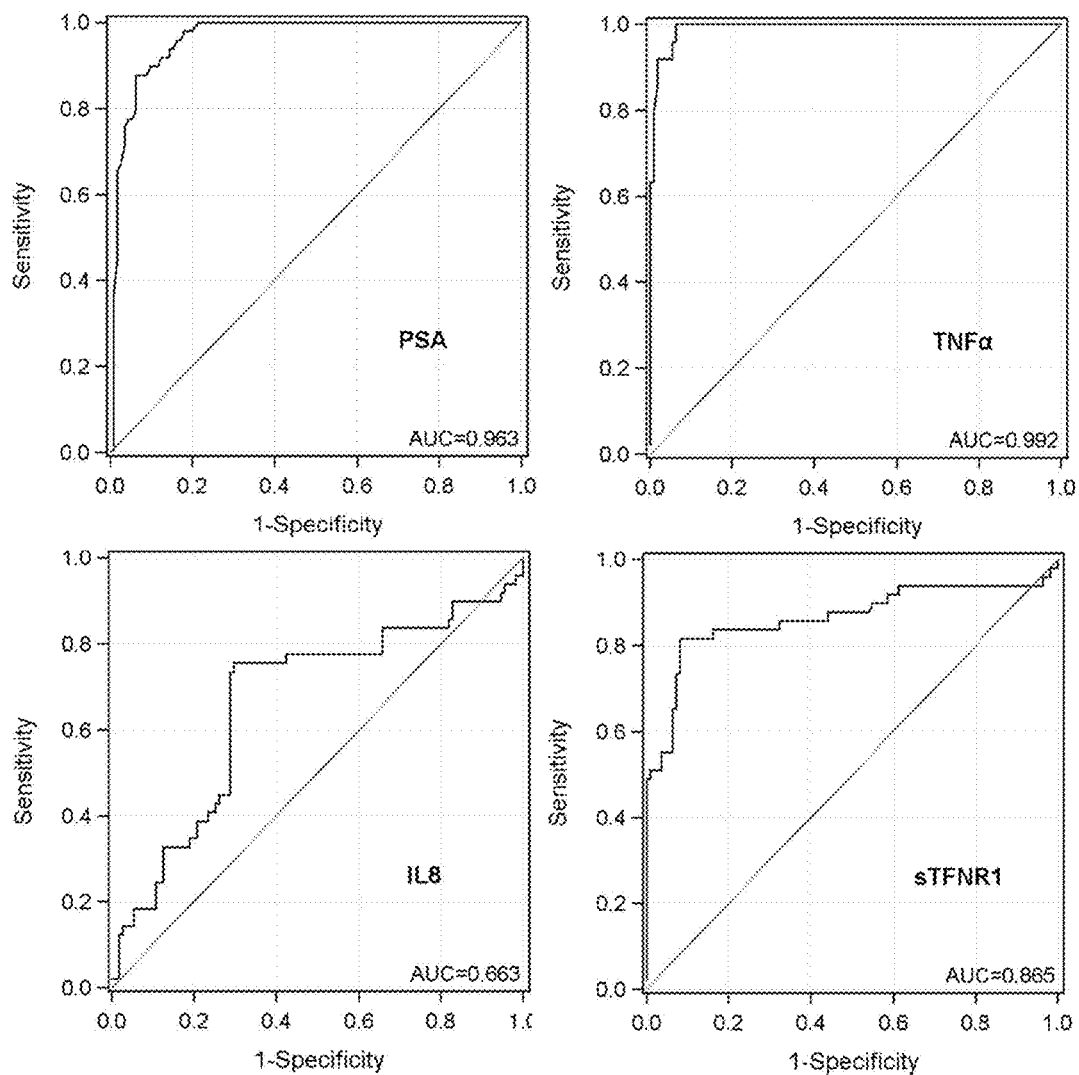
FIG. 2 provides graphical depictions of data depicting the probability of Local disease vs. metastatic CaP. This measure is equivalent to the area under the Receiver Operating Characteristic curve (AUC). TNFα and PSA were both very strong predictors of Local vs. Metastatic disease. sTNFr1 was a reasonably good predictor.

The ability of single analytes to distinguish between the localized CaP and CRPC patients is summarized in FIG. 2.

The strongest single predictors of localized versus metastatic CaP were TNF-α (AUC=0.992) and PSA (AUC=0.963) levels. Similar results for additive combinations of analytes are shown in Table 3, which shows AUC (95% CI) estimates for individual biomarkers and their combinations to distinguish between localized vs. metastatic CaP.

TABLE 3

| Markers | AUC (95%) |
|---|---|
| PSA | 0.963 (0.937 to 0.990) |
| IL-8 | 0.663 (0.566 to 0.761) |
| TNF-α | 0.992 (0.983 to 1.000) |
| sTNFR1 | 0.865 (0.788 to 0.942) |
| TNF-α & sTNFR1 | 0.993 (0.985 to 1.000) |
| TNF-α & PSA | 0.999 (0.998 to 1.000) |
| TNF-α & IL-8 | 0.992 (0.983 to 1.000) |
| sTNFR1 & PSA | 0.971 (0.950 to 0.993) |
| sTNFR1 & IL-8 | 0.870 (0.801 to 0.938) |
| PSA & IL-8 | 0.964 (0.938 to 0.990) |
| TNF-α & sTNFR1 & PSA | 0.999 (0.998 to 1.000) |
| TNF-α & sTNFR1 & IL-8 | 0.994 (0.985 to 1.000) |
| TNF-α & PSA & IL-8 | 0.999 (0.998 to 1.000) |
| sTNFR1 & PSA & IL-8 | 0.975 (0.957 to 0.994) |
| TNF-α & sTNFR1 & PSA & IL-8 | 0.999 (0.998 to 1.000) |

In order to quantify the impact of Gleason score on analyte activity, exploratory analyses were done on CRPC patients to study the impact of baseline characteristics on the cytokine expression measurements. The analyte values of patients with Gleason score of 8-10 did not differ from those with Gleason score of 2-7 (data not shown). Similarly, patients with performance status (PS) of zero did not differ from those with PS of 1-3 in their cytokine values, with the exception of PSA ($p=0.034$) (data not shown).

Example 3

An aspect of the present disclosure includes use of biomarkers that are specific and applicable in early diagnosis and management of CaP in both White American Men and African American Men. In connection with this, we tested sera from 28 normal healthy individuals of both races and analyzed for levels of IL-8; TNF-α and sTNFR1 by utilizing commercially available ELISA kits. The results as shown in Table 4, clearly indicate no major differences in levels of these biomarkers in the circulation among healthy African American men and White American Men.

TABLE 4

| Biomarker | White-men (n = 28) | African-American men (n = 28) | p-value |
|---|---|---|---|
| TNF-α | 3.78 | 3.47 | 0.256 |
| IL-8 | 6.49 | 5.82 | 0.177 |
| sTNFR1 | 381.85 | 379.96 | 0.696 |

Example 4

This Example demonstrates that combinations of markers discriminate between benign and malignant cases of CaP. As can be seen from Table 5, the AUC for each of the marker combinations was statistically superior to PSA alone ($p<0.01$ for each pairwise comparison). Each of the marker combination AUCs was significantly better than PSA alone ($p<0.01$ for all), but not statistically different from each other. In the observed data, combining TNF-α with PSA resulted in a 3.0-fold decrease in the PSA-Alone False Positive Fraction (FPF), and a 3.7-fold decrease in the PSA-Alone False Negative Fraction (FNF). The PSA+ sTNFR1 combination had a 5.9-fold decrease in the FPF, and a 2.5-fold decrease in FNF. Table 5 summarizes data obtained from assessments of the Benign/Malignant classification accuracy of the marker combinations based on ROC and Linear Discriminant Analysis (LDA) methods. In this retrospective sample, significant benefits were seen for combining TFN α or sTNFR1 with a PSA-based diagnostic test. The following abbreviations are used in Table 5: FPF: False Positive Fraction. The percentage of truly Benign patients misclassified as Malignant. FNF: False Negative Fraction. The percentage of truly Malignant patients classified as Benign. Overall: The overall percentage of patients who were misclassified.

TABLE 5

| AUC Estimates | | | |
|---|---|---|---|
| Marker Combination | AUC (95% Confidence Interval) | | |
| PSA Alone | 0.81 (0.73 to 0.89) | | |
| PSA + IL8 | 0.96 (0.93 to 0.99) | | |
| PSA + TNFα | 0.97 (0.95 to 0.99) | | |
| PSA + sTNFR1 | 0.98 (0.94 to 1.0) | | |
| LDA Classification Error Rates | | | |
| Marker Combination | FPF | FNF | Overall |
| PSA Alone | 23.1% | 40.3% | 31.7% |
| PSA + IL8 | 23.1% | 35.3% | 29.2% |
| PSA + TNFα | 7.7% | 10.8% | 9.2% |
| PSA + sTNFR1 | 3.9% | 14.4% | 9.1% |

Example 5

This Example provides a description of data obtained from assessments of the Local/CRPC classification accuracy of the marker combinations based on ROC and Linear Discriminant Analysis (LDA) methods. In this retrospective sample, significant benefits were seen for combining TNF-α with a PSA-based diagnostic test. The results are summarized in Table 6.

TABLE 6

| AUC Estimates | | | |
|---|---|---|---|
| Marker Combination | AUC (95% Confidence Interval) | | |
| PSA Alone | 0.98 (0.96 to 0.99) | | |
| PSA + IL8 | 0.99 (0.98 to 1.0) | | |
| PSA + TNα | 0.99 (0.99 to 1.0) | | |
| PSA + sTNFR1 | 0.99 (0.98 to 1.0) | | |
| LDA Classification Error Rates | | | |
| Marker Combination | FPF | FNF | Overall |
| PSA Alone | 0.0% | 19.2% | 9.6% |
| PSA + IL8 | 0.0% | 17.3% | 8.7% |
| PSA + TNFα | 0.0% | 3.9% | 1.9% |
| PSA + sTNFR1 | 2.9% | 14.4% | 8.6% |

As can be seen from Table 6, the AUC for PSA+TNF-α was statistically superior to PSA alone ($p=0.04$). AUCs for the other marker combination were not statistically different from PSA Alone. PSA Alone, PSA+IL8 and PSA+TNF α correctly identified 100% of the Local Disease cases (FPF=0). PSA+TNF-α was less likely than the other combinations to misdiagnose a truly CRPC patient as having Local Disease (FNF=3.9% vs>14%).

Example 6

Based on the foregoing description, the present disclosure includes aiding in diagnosis as described herein via adaptation of statistical analysis for biomarker combinations as generally described in Etzioni, R., C. Kooperberg, M. S. Pepe, R. Smith, and P. H. Gann (2003, October). *Biostatistics* 4 (4), 523-538. In particular, for each marker, ten threshold values were identified using the observed decile limits. In one illustrative embodiment, A, B, C denotes a set of decile limits for IL8, TNFa and sTNFr1 respectively, in the following diagnostic rule forms which are intended to demonstrate but not limit the disclosure:

$$(IL8 \geq A \text{ and } TNFa \geq B \text{ and } sTFNr1 \geq C) = \begin{cases} \text{True} & \text{Malignant disease} \\ \text{False} & \text{Local disease} \end{cases}$$

$$\text{and } (IL8 \leq A \text{ and } TNFa \geq B \text{ and } sTFNr1 \geq C) = \begin{cases} \text{True} & \text{Local disease} \\ \text{False} & \text{Benign disease} \end{cases}$$

We applied these rules to distinguish local disease from metastatic disease, and local disease versus benign disease, as follows.

Local vs Metastatic rules had the form (IL8>=A and TNFa>=B and sTFNr1>=C). Patients testing positive by this rule were classified as Metastatic; the remaining patients were classified as Local. Benign and Control patients were excluded from this analysis.

Local vs Benign rules had the form (IL8<=A and TNFA>=B and sTFNr1>=C). Patients testing positive by this rule were classified as having Local disease; the remaining patients were classified as Benign. Metastatic and Control patients were excluded from this analysis.

Each rule form had up to 10×10×10=1000 possible decile threshold combinations. For each combination, the proportion of correctly classified patients within each disease group was calculated. These proportions are often referred to as sensitivity and specificity. The final diagnostic rules were identified using the Youden Index, calculated as Youden Index=Sensitivity+Specificity−1. Larger values of the Youden Index are generally preferred. By using this analysis we obtained the following results.

The Local vs Metastatic diagnostic rules had the form (IL8>=A and TNFa>=B and sTFNr1>=C). For various values of (A,B,C), Table 7 shows the proportions of Metastatic and Local disease patients who were correctly classified, and the corresponding Youden index. Table 7 focuses on threshold combinations that correctly classified at least 80% of the Metastatic and 80% of the Local disease patients. The threshold combination with the highest Youden index is shown in enlarged and bolded text.

TABLE 7

| Marker Threshold for Metastatic Disease (vs Local Disease) | | | % Correctly Classified | | |
| --- | --- | --- | --- | --- | --- |
| IL8 | TNFa | sTNFr1 | Mets | Local | Youden |
| >=5.1 | >=1.7 | >=1221.7 | 91.89 | 83.67 | 0.76 |
| >=5.1 | >=2.5 | >=1029.6 | 94.59 | 83.67 | 0.78 |

TABLE 7-continued

| Marker Threshold for Metastatic Disease (vs Local Disease) | | | % Correctly Classified | | |
| --- | --- | --- | --- | --- | --- |
| IL8 | TNFa | sTNFr1 | Mets | Local | Youden |
| >=5.1 | >=2.5 | >=1221.7 | 91.89 | 87.76 | 0.80 |
| >=5.1 | >=3.1 | >=513.9 | 96.40 | 91.84 | 0.88 |
| >=5.1 | >=3.1 | >=837.7 | 96.40 | 91.84 | 0.88 |
| >=5.1 | >=3.1 | >=1029.6 | 91.89 | 95.92 | 0.88 |
| >=5.1 | >=3.1 | >=1221.7 | 89.19 | 97.96 | 0.87 |
| >=5.1 | >=4.1 | >=513.9 | 86.49 | 100.00 | 0.86 |
| >=5.1 | >=4.1 | >=837.7 | 86.49 | 100.00 | 0.86 |
| >=5.1 | >=4.1 | >=1029.6 | 81.98 | 100.00 | 0.82 |
| >=10.2 | >=0.8 | >=1221.7 | 82.88 | 83.67 | 0.67 |
| >=10.2 | >=1.7 | >=1221.7 | 82.88 | 87.76 | 0.71 |
| >=10.2 | >=2.5 | >=1029.6 | 83.78 | 85.71 | 0.69 |
| >=10.2 | >=2.5 | >=1221.7 | 82.88 | 89.80 | 0.73 |
| >=10.2 | >=3.1 | >=513.9 | 86.49 | 91.84 | 0.78 |
| >=10.2 | >=3.1 | >=837.7 | 86.49 | 91.84 | 0.78 |
| >=10.2 | >=3.1 | >=1029.6 | 81.98 | 95.92 | 0.78 |
| >=10.2 | >=3.1 | >=1221.7 | 81.08 | 97.96 | 0.79 |

From this analysis the disclosure provides the following approach: In an individual known or suspected to have either Local or Metastatic disease, marker expression values indicate metastatic disease if: IL8>=5.1 pg/ml, TNFa>=3.1 pg/ml and sTNFr1>=513.9 pg/ml. This approach correctly identified (96.40%, 91.84%) of the Metastasis and Local disease patients respectively. If the sTFNr1 threshold is increased to 1029.6 pg/ml, the correctly identified proportions change to (91.89%, 95.92%).

Figure 3:
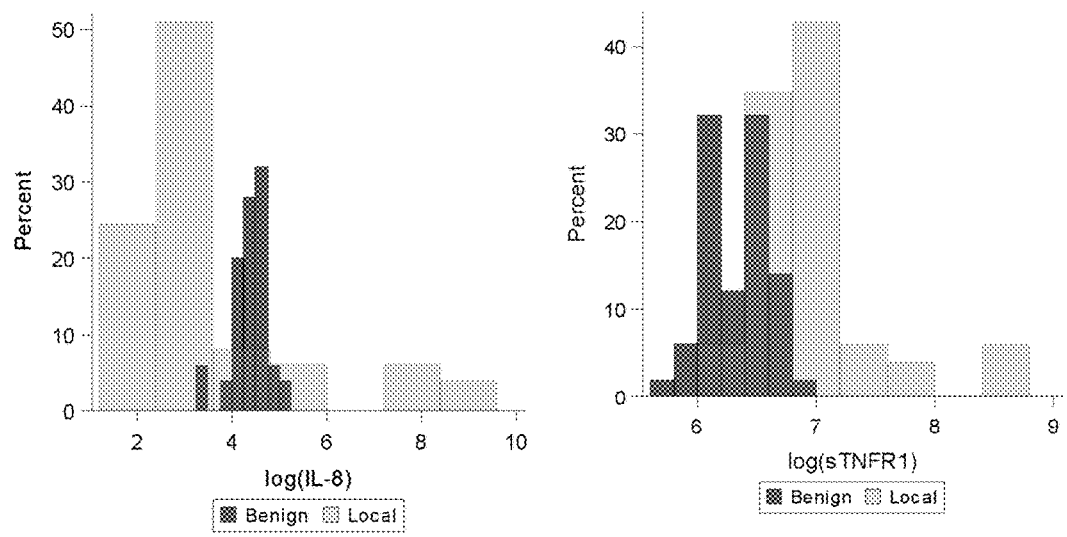
FIG. 3 provides histograms of log-transformed IL8 and sTNFr1 in the Benign and Local disease patients.

The Local vs Benign diagnostic approach uses the form (IL8<=A and TNFa>=B and sTNFr1>=C). The logic for this rule form is shown in FIG. 3. Among the Benign patients, IL8 was tightly clustered in the middle of the overall range, and in the middle of range among Local patients. The distributions of TNFa and sTNFr1 had similar characteristics, so TNFa is not shown. Table 8 shows the proportion of Benign and Local patients who were correctly classified, and the corresponding Youden index, for several possible threshold combinations. These combinations had the highest Youden index available. In Table 8, the proportion of Local and Benign patients who were correctly classified using various IL8, TNFa and sTNFr1 expression thresholds. The diagnostic rule was formulated as (IL8<=A and TNFa>=B and sTNFr1>=C). A positive test result indicates Local disease.

TABLE 8

| Marker Threshold for Local Disease (vs Benign) | | | % Correctly Classified | | |
| --- | --- | --- | --- | --- | --- |
| IL8 | TNFa | sTNFr1 | Benign | Local | Youden |
| <=42.5 | | | 94% | 77.6% | 0.72 |
| | >=1.4 | | 66% | 87.7% | 0.54 |
| | | >=729 | 80% | 81.6% | 0.62 |
| <=7322 | >=1.2 | >=729 | 92% | 79.6% | 0.72 |
| <=7322 | >=1.4 | >=729 | 94% | 77.6% | 0.72 |

As will be evident from Table 8, by itself, IL8 provided good classification accuracy (94% Benign and 77.6% Local). In combination, TNFa and sTNFr1 tended to dominate IL8. In our sample, the maximum value of IL8 was 7322. Individually, TNFa and sTNFr1 were fairly good classifiers. From this analysis the disclosure includes the following approach: For an individual that is known or suspected to have either Local or Benign disease, this disclosure aids in diagnosis of Local disease if his (TNFa>=1.2 pg/ml and sTFNr1>=729 pg/ml).

Although the disclosure has been described in detail for the purposes of illustration, it is understood that such detail is solely for that purpose, and variations can be made therein by those skilled in the art without departing from the spirit and scope of the disclosure.

We claim:

1. A kit for use in immunological detection of tumor necrosis factor α(TNFα), soluble TNF receptor 1 (sTNFR1), interleukin-8 (IL-8), and Prostate Serum Antigen (PSA), wherein the kit comprises one or more sealed containers that comprise monoclonal and/or polyclonal capture antibodies that are specific for TNFα, sTNFR1, IL-8, and PSA, and wherein the kit comprises one or more sealed containers that comprise monoclonal and/or polyclonal detection antibodies that are for use in specifically binding to captured TNFα, sTNFR1, IL-8, and PSA.

2. The kit of claim 1, wherein the capture antibodies are fixed to a substrate.

3. The kit of claim 1 further including printed material which provides an indication that that an amount of IL-8 that is equal to or greater than a reference amount, that an amount of TNFα equal to or greater than a reference amount, and that an amount of sTNFR1 equal to or greater than a reference amount, aids in a diagnosis that the individual has metastatic prostate cancer; and/or wherein the printed material provides an indication that an amount of TNFα equal to or greater than a reference amount and an amount of sTNFR1 equal to or greater than a reference amount aids in a diagnosis that the individual has localized prostate cancer.

* * * * *